United States Patent [19]

McGredy

[11] Plant 5,142

[45] Nov. 22, 1983

[54] ROSE PLANT MACCANTER

[76] Inventor: Samuel D. McGredy, P.O. Box 14100, Panmure, Auckland, New Zealand

[21] Appl. No.: 392,548

[22] Filed: Jun. 28, 1982

[51] Int. Cl.[3] ..... A01H 5/00

[52] U.S. Cl. ..... Plt./20

[58] Field of Search ..... PLT./20

*Primary Examiner*—Robert E. Bagwill
*Attorney, Agent, or Firm*—Vincent G. Gioia

[57] ABSTRACT

A new grandiflora rose variety of bright currant red coloring which is unfading and of good form.

1 Drawing Figure

1

The present invention relates to a new and distinct variety of rose plant of the hybrid tea rose class, which was originated by my crossing as seed parent the rose known as "Kalahari" and the rose known as "John Waterer" as pollen parent. The denomination of the new variety is Maccanter.

Among the novel characteristics possessed by this new variety which distinguish it from its parents and all other varieties of which I am aware are bright currant red flowers with good color retention upon aging and good form. Relatively low petal count and virtual absence of petalloids allow large, numerous stamens to show to advantage as blooms open fully. New growth is showy wine red and plant is very vigorous producing numerous new basals annually. Blooms may be borne one to a stem and in sprays in spring but in late summer capable of producing large panicles with 12 to 25 blooms. Many of the longer stems in each panicle have several leafy bracts making them useful as cut blooms. Asexual reproduction by budding of the new variety as performed in Clackamas County, Oreg., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "46A" is plate 46A of The Royal Horticultural Society Colour Chart.

Parentage: Seedling.
*Seed parent.*—"Kalahara".
*Pollen parent.*—"John Waterer".
Class: Grandiflora.

The following observations are made of specimens grown under glass in Clackamas County, Oreg. during the month of May.

1. FLOWER

Blooming habit: Continuous.

A. Bud:
(1) *Size.*—Medium.
(2) *Form.*—High centered, long pointed.

2

(3) *Color.*—After sepals fall, near 46A. When sepals begin to unfurl, 45A.
(4) *Sepals.*—Longer than bud, simple glabrous outside; inside and edges, wooly.
(5) *Peduncle.*—Length — Long. Aspect — Straight. Strength — Erect. Color — Near 144B.

B. Bloom:
(1) *Size.*—Average size when fully expanded — about 4½ inches.
(2) *Borne.*—Singly in spring, large trusses and sprays in summer and fall.
(3) *Form.*—High centered, slightly flaring with slight quilling at maturity, stamens show at center.
(4) *Petalage.*—Number of petals under normal conditions — about 24.
(5) *Color.*—Currant red coloring of buds continues as petals unfurl changing only slightly to 46B as flower opens to ½ open stage. Stark white streaking may be seen in some outer petals. Vibrant coloring remains constant as blooms open further until full open stage when stamens are visible. Petal undersurface is near 53B. General tonality from a distance is 46B.

C. Petals:
(1) Texture.—Thick.
(2) *Appearance.*—Inside very velvety, reverse satiny.
(3) *Form.*—Fan shaped, reflex as flower opens.
(4) *Arrangement.*—Regular.
(5) *Petaloids in Center.*—Few to none.
(6) *Persistence.*—Drop off cleanly.
(7) *Fragrance.*—Slight.
(8) *Lasting quality.*—Long lasting on plant and as cut flower.

2. REPRODUCTIVE ORGANS

A. Stamens, filaments and anthers:
*Arrangement.*—Numerous stamens regularly arranged around styles, long filaments 33A, anthers large, showy 13C.

B. Pollen:
*Color.*—Near 13C.

C. Styles: Many, regular in length, 13D at base, 40D at top, heavily contorted.

D. Stigmas:
Color.—Near 13C, surface broad, spongy.

E. Hips: Large, globular, ⅝ to ¾ inch, color 33B, seeds protrude.

3. PLANT

A. Form: Upright.

B. Growth: Very vigorous, with numerous basals annually.

*Height attained.*—About 5½ feet.

C. Foliage: Compound 5 to 7 leaflets, mostly 5.

(1) *Size.*—Large.

(2) *Quantity.*—Abundant.

(3) *Color.*—New foliage: Upper side — Wine red, near 187A. Under side — Slightly lighter than upper side. Old foliage: Upper side — Near 139A. Under side — Near 146B.

(4) *Shape.*—Oval, pointed.

(5) *Texture.*—Upper side is shiny and under side is matte.

(6) *Edge.*—Serrated.

(7) *Serration.*—Simple.

(8) *Leaf stem.*—Color — Near to 152B. Under side — Near 146B.

(9) *Stipules.*—Medium, narrow.

(10) *Resistance to disease.*—Blackspot — Average. Mildew — Excellent. Rust — Excellent.

D. Wood:

(1) *New wood.*—Color — Near 187A. Bark — Smooth.

(2) *Old wood.*—Color — near 146B. Bark — Smooth.

E. Thorns:

(1) *Thorns.*—Quantity (main stalk) — Few, broad to point, large, near 60A when young. On laterals from stalk — Few.

(2) *Prickles.*—None.

F. Winter hardiness: Needs protection in severe climate.

I claim:

1. A new and distinct variety of rose plant of the grandiflora rose class, substantially as shown and described, characterized particularly by currant red buds and flowers retaining color vibrancy upon aging borne one to a stem and in sprays but being capable of producing panicles of 12 to 25 blooms in late summer.

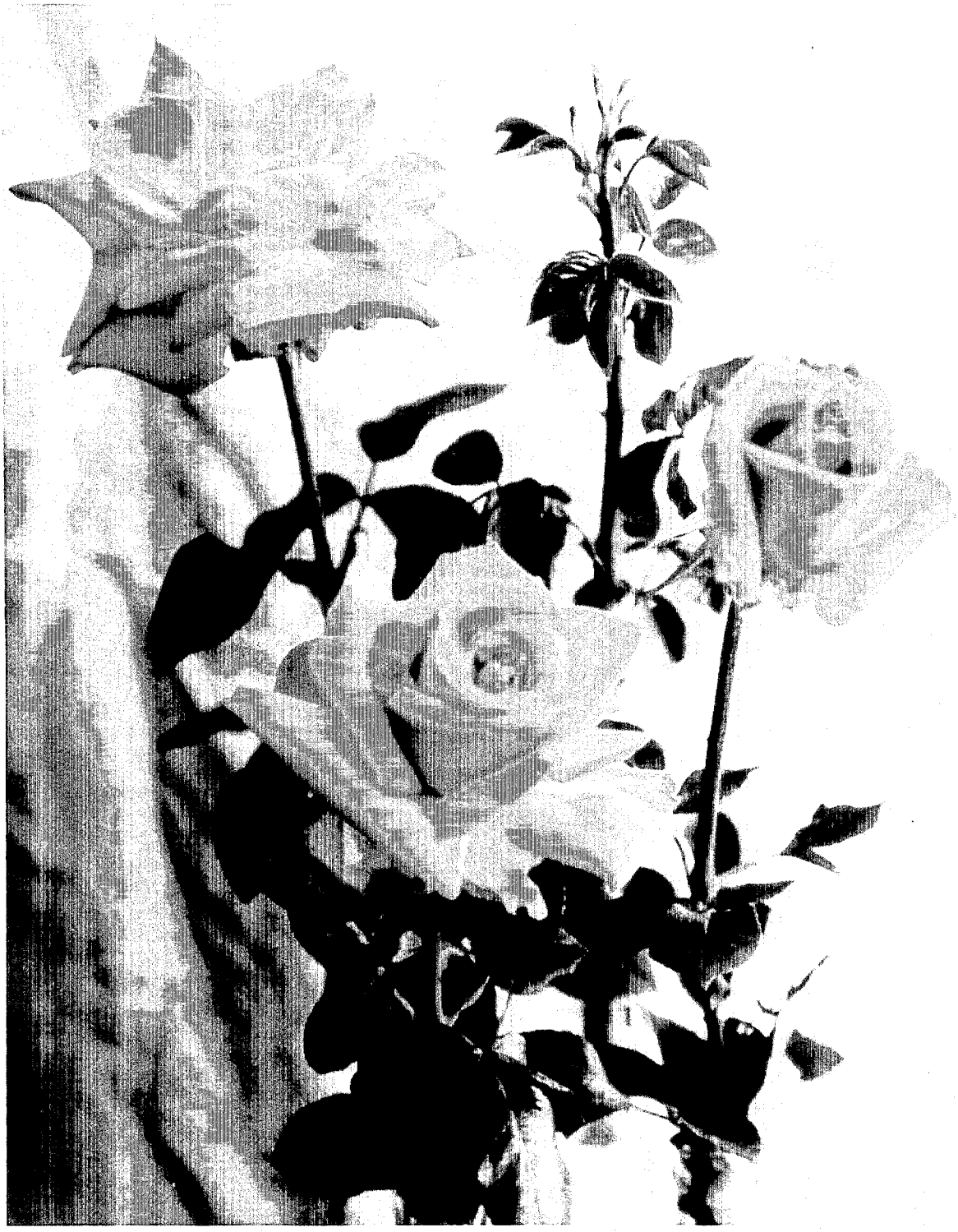

* * * * *